United States Patent [19]

Kupershmidt

[11] Patent Number: 5,398,681
[45] Date of Patent: Mar. 21, 1995

[54] POCKET-TYPE INSTRUMENT FOR NON-INVASIVE MEASUREMENT OF BLOOD GLUCOSE CONCENTRATION

[75] Inventor: Vladimir Kupershmidt, Pleasonton, Calif.

[73] Assignee: Sunshine Medical Instruments, Inc., Calif.

[21] Appl. No.: 7,568

[22] Filed: Jan. 22, 1993

Related U.S. Application Data

[63] Continuation-in-part of Ser. No. 988,715, Dec. 10, 1992, abandoned.

[51] Int. Cl.$^6$ .............................................. A61B 5/00
[52] U.S. Cl. ................................. 128/633; 128/665; 356/364; 356/368
[58] Field of Search ................. 356/364, 366, 368, 47; 128/633, 664–665

[56] References Cited

U.S. PATENT DOCUMENTS

| | | | |
|---|---|---|---|
| 4,008,717 | 2/1977 | Kowarski | 128/214 R |
| 4,055,175 | 10/1977 | Clemens et al. | 128/213 |
| 4,240,438 | 12/1980 | Updike et al. | 128/635 |
| 4,401,122 | 8/1983 | Clark, Jr. | |
| 4,458,686 | 7/1984 | Clark, Jr. | 128/635 |
| 4,551,427 | 11/1985 | Draeger et al. | 435/14 |
| 4,627,445 | 12/1986 | Garcia et al. | 128/770 |
| 4,633,087 | 12/1986 | Rosenthal et al. | 250/341 |
| 4,633,878 | 1/1987 | Bombardieri | 128/635 |
| 4,685,463 | 8/1987 | Williams | 128/632 |
| 4,704,029 | 11/1987 | Van Heuvelen | 356/39 |
| 4,750,496 | 6/1988 | Reinhart et al. | 128/635 |
| 4,834,532 | 5/1989 | Yount | 356/41 |
| 4,875,486 | 10/1989 | Rapoport et al. | 128/653 |
| 4,882,492 | 11/1989 | Schlager | 250/346 |
| 4,882,493 | 11/1989 | Lodder et al. | 250/353 |
| 4,901,728 | 2/1990 | Hutchison | 128/633 |
| 4,969,115 | 11/1990 | Rosenthal | 364/571.03 |
| 4,975,581 | 12/1990 | Robinson et al. | 250/339 |
| 4,990,772 | 2/1991 | Rosenthal | 250/252.1 |
| 5,009,230 | 4/1991 | Hutchinson | 128/633 |
| 5,028,787 | 7/1991 | Rosenthal et al. | 250/341 |
| 5,034,189 | 7/1991 | Cox et al. | 422/52 |
| 5,054,487 | 10/1991 | Clarke | 128/633 |
| 5,059,394 | 10/1991 | Phillips et al. | 422/68.1 |
| 5,070,874 | 12/1991 | Barnes et al. | 128/633 |

(List continued on next page.)

OTHER PUBLICATIONS

Kozaitis et al. "Laser Polarimetry For Measurement Of Drugs In The Aqueous Humor", Annual International Conference of the IEEE Engineering in Medicine and Biology Society, vol. 13, No. 4, 1991, pp. 1570–1571.

(List continued on next page.)

*Primary Examiner*—Lee S. Cohen
*Assistant Examiner*—Robert L. Nasser, Jr.
*Attorney, Agent, or Firm*—Davis Hoxie Faithfull & Hapgood

[57] ABSTRACT

A pocket-type apparatus for non-invasive measurement of blood glucose concentration based on producing a polarized-modulated laser beam via an optical phase shifter (32), measuring a phase difference introduced, e.g., by a finger (F) or a ear lobule (E) of a subject, measuring phase difference between a reference signal (SR) and a measurement signal (SM), and processing the obtained data which are then presented as blood glucose concentration. The optical phase shifter (32) comprises a pair of fiber-optic arms (40 and 42). The laser beam is fed to one of the fiber-optic arms (4), then both arms are guided through an input optical coupler (44) which splits the laser beam into a first component, which further propagates through the first optic-fiber arm (40), and a second component, which propagates through second optic-fiber arm (42). An optical phase shifter (48) which is attached to the first fiber-optic arm (40) modulates the first component of the laser beam. Both arms are then guided through an output optical coupler (46) which coherently mixes the light-propagating modes of the fiber-optic arms so that the output of each arm has a complementary coherent mixture of the beam first and second components with an orthogonal direction of polarization. An output of one of the fiber-optic arms is used as a reference optical signal and an output of the other fiber-optic arm is used as a measuring optical signal.

27 Claims, 7 Drawing Sheets

U.S. PATENT DOCUMENTS

| | | | |
|---|---|---|---|
| 5,072,732 | 12/1991 | Rapoport et al. | 128/653.2 |
| 5,077,476 | 12/1991 | Rosenthal | 250/341 |
| 5,086,229 | 2/1992 | Rosenthal et al. | 250/341 |
| 5,127,405 | 7/1992 | Alcala et al. | 128/633 |
| 5,127,406 | 7/1992 | Yamaguchi | 128/633 |
| 5,137,023 | 8/1992 | Mendelson et al. | 128/633 |
| 5,168,326 | 12/1992 | Tokieda et al. | 356/368 |
| 5,181,138 | 1/1993 | Davis et al. | 359/239 |
| 5,209,231 | 5/1993 | Cote et al. | 128/633 |
| 5,222,496 | 6/1993 | Clarke et al. | 128/633 |
| 5,243,983 | 9/1993 | Tarr et al. | 128/633 |
| 5,289,258 | 2/1994 | Szafraniec et al. | 356/350 |

OTHER PUBLICATIONS

Arnold et al., "Determination of Physiological Levels of Glucose in a Aqueous Matrix with Digitally Filtered Fourier Transform Near Infrared Spectra", *Anal. Chem.*, vol. 62, No. 14, Jul. 15, 1990, pp. 1457–1464.

Cote et al. "Laser Polarimetry For Glucose Monitoring", Annual International Conference of the IEEE Engineering in Medicine and Biology Society, vol. 12, No. 2, 1990, pp. 476–477.

Cote et al. "Optical Polarimetric Sensor for Blood Glucose Measurement" IEEE 1990, pp. 101–102.

March et al., "Optical Monitor of Glucose", vol. XXV Trans. Am. Soc. Artif. Intern. Organ., 1979, pp. 28–31.

Hobbs, "Fluorescence Reveals Toxins on Antibody-Coated Fiberoptic Probe" Laser Focus World, May 1992 pp. 83–86.

Lakowicz, "Fluorescence Lifetime Sensing Generates Cellular Images" Laser Focus World, May 1992, pp. 60–62, 65, 66, 68, 70, 72, 75, 77–79 80.

Cote et al., "Noninvasive Optical Polarmetric Glucose Sensing Using True Phase Measurement Technique" IEEE Transactions on Biomedical Engineering, vol. 39, No. 7, Jul. 1992, pp. 752–756.

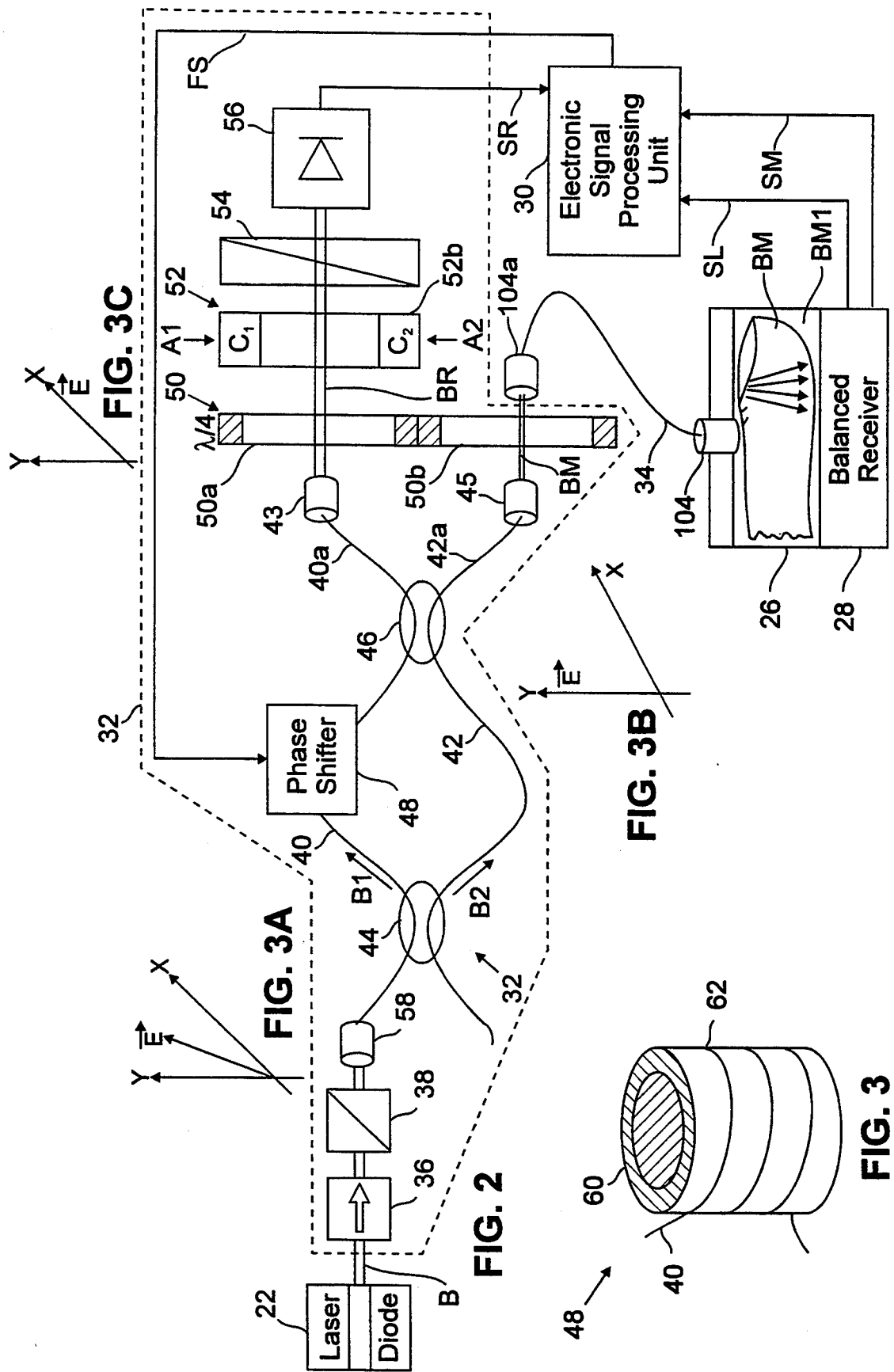

POCKET-TYPE INSTRUMENT FOR NON-INVASIVE MEASUREMENT OF BLOOD GLUCOSE CONCENTRATION

CROSS REFERENCE TO RELATED APPLICATIONS

This application is a continuation-in-part of U.S. patent application Ser.No. 07/988,715, filed Dec. 10, 1992, in the name of Vladimir Kupershmidt and entitled Methods and Apparatus for Non-Invasive Phase-Sensitive Measurement of Blood Glucose Concentration now abandoned.

FIELD OF THE INVENTION

The present invention relates to measuring the concentration of glucose in the medical field, more particularly to the non-invasive, phase-sensitive measurement of the glucose concentration in blood.

BACKGROUND OF THE INVENTION

As of 1992, more than ten million people in the United States of America suffer from diabetes (an increased level of glucose in the blood) and hypoglycemia (a reduced level of glucose in the blood). Individuals afflicted with either disease in a severe form typically perform an invasive blood glucose level analysis four or more times a day.

Invasive techniques require withdrawal of a blood sample from the patient each time an analysis is to be performed. An accurate laboratory blood analysis requires withdrawing from 5 to 10 ml of blood and analyzing it using a laboratory instrument designed for performing such a biochemical analysis. However, the results of the test often are not available for several hours, and sometimes days. In addition, the instruments necessary to perform such an analysis are expensive and require that the blood samples be taken and analyzed by trained technicians.

Another invasive technique, referred to as a "finger poke" or a "finger stick" uses an integrated, self-contained instrument that evaluates a much smaller blood sample (approximately 0.25 ml). The small blood sample is obtained by puncturing a finger with a small lancet. The sample is then placed on a chemically treated carrier and inserted into the instrument. The finger poke devices normally provide the glucose concentration results in a few moments. However, they are still quite costly for private use, i.e., in the range of several thousand dollars.

More recently, portable finger poke instruments have become available which require the use of single use, disposable, chemically treated carrier "strips." Although the portable instruments have a relatively low cost (about $100 to $300), the cumulative cost to diabetics for the normal supply of disposable carrier "strips" is considerable.

Invasive techniques for glucose analysis are problematic and suffer from poor patient compliance. Many people who would benefit from knowing their glucose concentration are reluctant to have blood withdrawn by a finger poke or a hypodermic needle or have a generalized fear of invasive medical procedures. Still others suffer anxiety in connection with the sampling and worry about the discomfort (pain) and possibility of infection. Another problem is that frequent invasive glucose testing uses up convenient sample sites and complicates further testing until the used convenient sites heal.

Non-invasive methods for measuring blood constituents, including glucose have been described. However, to date none of these techniques has resulted in a commercially useful instrument. The non-invasive monitoring methods are roughly divided into measurements based on either the intensity of light being transmitted through or reflected from the tissue, or the phase shift of modulated light transmitted through the tissue (the "phase-sensitive" measurement).

When light is transmitted through perfused tissue in vivo, e.g., through a patient's finger, it is differently absorbed by the various components illuminated, namely blood, with its many constituent parts, tissue (including protein, fat, water, cholesterol, etc.), cartilage, and bone. The different components thus form an absorption spectrum for each wavelength. The total absorption of a given wavelength of light by all of the components is called "real absorption" and the absorption spectrum may vary for different wavelengths.

The known intensity sensing methods for measuring the level of a blood constituent, including glucose, are based on measuring a real absorption spectrum for blood perfused tissue at two or more different wavelengths, and subtracting therefrom the statistical absorption spectra for each of the various blood components, except for the one component being measured. It is assumed that after such subtraction, the remainder is a real spectrum of the constituent to be measured.

Rosenthal et al. U.S. Pat. No. 5,086,229 refers to such a non-invasive, near-infrared quantitative analysis instrument for measuring blood glucose. The instrument contains a plurality of near-infrared laser sources having different wavelengths of emission and one or a plurality of photodetectors. A blood-containing part, e.g., a finger, is placed between the laser sources and photodetectors. The light sources are illuminated and the wavelengths then transmitted through the blood-containing part are detected. The real absorption spectrums obtained from the photodetector signals are compared with individual statistical absorption spectra of each constituent, which are stored in the memory of the instrument. A glucose level is derived from the comparison.

The intensity measuring instruments, including the Rosenthal instrument, suffer from the following disadvantages. First, because they measure intensity, the noise level of the measured signal is affected by components of the tissue other than blood, and variations in conditions such as background light, tissue temperature, ambient temperature, and the amplitude of the laser source. This results in a poor signal-to-noise ratio. Even the use of the latest low-noise electronics would not substantially improve this ratio.

Second, because the subtraction technique is based on statistically derived absorption data for each individual constituent, the results obtained are of necessity statistical. However, the differences between the actual glucose level in blood and the results of statistical measurements may be substantial and significant. In this regard, the absorption due to the glucose concentration is very small compared to other components such that statistical errors may be a greater component of the determined value than the actual glucose component.

The non-invasive phase sensitive measurement methods possess significantly higher sensitivity and a much higher signal-to-noise ratio than intensity-measurement methods. The higher sensitivity is the consequence of the noise sources affecting the amplitude, but not the phase, of a signal.

In phase sensitive techniques, an instrument compares a known reference signal, e.g., a sine wave, with a measurement signal that has been passed through the tissue. The measurement signal will have a time delay (phase shift) relative to the reference signal because of various factors, e.g., a fluorescence time delay, etc. Concentrations of blood constituents then may be obtained from a measurement of the time delay (phase shift).

Cote et al., "Noninvasive Optical Polarimetric Glucose Sensing Using A True Phase Measurement Technique," *IEEE Transactions of Biomedical Engineering,* Vol. 39, No. 7, July 1992, pp. 752–756 ("Cote") refers to passing linearly-polarized light through the anterior chamber of an excised human eye and determining the glucose level of the aqueous eye humor based on the phase shift between the reference signal and the measurement signal that was converted by the glucose. A helium-neon laser beam, coupled through a rotating linear polarizer along with two stationary linear polarizers and two detectors, is used to produce reference and signal outputs. The polarizer was rotated by means of a synchronous electric motor. The amplitudes of these outputs varied sinusoidally with a frequency twice that of the angular velocity of the rotating polarizer. The phase difference of the outputs would be proportional to the rotation of the linear polarization vector passing through the anterior chamber of the eye.

One problem with the Cote apparatus is that it uses a synchronous motor which generates mechanical vibrations which cannot exceed, e.g., 200 Hz. Therefore, the frequency of rotation of the motor falls into the frequency range (1 Hz to 600 Hz) of mechanical vibrations produced by different sources, interferes with those mechanical vibrations, and produces high measurement noise. Consequently, the Cote technique can be implemented only under laboratory conditions where mechanical vibrations can be isolated, and is unsuitable for application in the form of a portable instrument for personal use.

Another problem with the Cote measurement system is that it is based on passing the light through the human eye. It is thus inconvenient for practical self-administration of the test. More important, however, is that the eye is subject to involuntary movements (such as microsaccadic movements) which fall into the same frequency range as the rotating frequency of the driving motor of the system and have amplitudes of 1 to 3 min of arc. Should the apparatus be used in vivo, such involuntary eye movements would lead to interference with the measurement signals and would markedly increase the measurement noise.

Still another problem with the Cote system is that the axis of the synchronous motor can be fixed with respect to the direction of propagation of optical signals with an accuracy not exceeding several minutes of arc. This means that using the device requires that a calibration be carried out in real time.

Thus, there is a continuing need for improved non-invasive analytical instruments and methods that would provide essentially the same accuracy as conventional invasive blood glucose tests. There also is a need for non-invasive, low-cost methods and instruments for the measurement of glucose levels in diabetic or hypoglycemic patients. There also is a need for a durable, cost-effective, and environmentally conscious nondisposable apparatus for measuring blood glucose.

The applicant has developed a method and apparatus for non-invasive measurement of blood glucose concentration which is described in said parent U.S. patent application Ser. No. 08/071,321 now pending and commonly assigned, the disclosure of which is incorporated herein by reference in its entirety. These methods and apparatus are based on producing a phase-modulated laser beam via a polarizing frequency shifter, measuring a phase difference introduced, e.g., by a finger or a ear lobule of a subject, measuring phase difference between a reference signal and a probe signal, and processing the obtained data which are then presented as blood glucose concentration.

Although the inventions described in said parent U.S. Ser. No. 08/071,321 make it possible to produce high-resolution non-invasive optical measurements of the blood glucose concentration, and thus overcome the deficiencies of the prior art, the apparatus disclosed uses a polarizing frequency shifter which is based on the use of bulk optics (crystal optics) which is expensive. In addition, an apparatus which contains a bulk-optic type polarizing frequency shifter cannot be produced in small dimensions because its polarizing frequency shifter cannot be manufactured in an integrated-optic implementation. The present invention is directed to an improvement of the methods and apparatus disclosed in the aforementioned U.S. patent application.

SUMMARY OF THE INVENTION

It is, therefore, an object of the invention to overcome the disadvantages of existing non-invasive instruments and to provide improved methods and apparatus for the non-invasive phase-sensitive measurement of blood constituents such as glucose.

It is another object of the invention to provide a non-invasive apparatus for measuring blood constituents including glucose based on phase-sensitive measurements that is free of moving mechanical parts, results in low noise measurements, and operates in the frequency range beyond that of mechanical vibrations.

It is another object to provide a portable, non-invasive blood glucose monitor that is suitable for personal use, at home or away.

It is another object to provide a portable blood-monitoring device which obtains glucose level measurements through high-scattering (signal-depolarizing) tissue, and is not restricted for use with the eye. It is another object to provide a non-invasive instrument that obtains glucose level measurements using blood-carrying body parts such as fingers, toes, and earlobes.

It is another object of the present invention to eliminate the above disadvantages of existing non-invasive instruments and to provide an instrument for the non-invasive phase-sensitive measurement of blood glucose level which is small in size and can be produced in integrated-optic implementation.

Broadly, the invention concerns apparatus and methods for the non-invasive measurement of the concentration of a constituent in blood based on precision, phase sensitive and high signal to noise measurements.

One aspect of the invention is directed to a method and apparatus for the non-invasive precision phase sensitive measurement of the glucose level in the blood. One such method includes the steps of:

passing a beam emitted by an infrared laser beam source through an optical phase modulator that is fiber-optic based and driven by a piezoceramic transducer and produces two polarized-modulated beams, each having a direction of polarization rotating in the plane of polarization with a frequency of rotation falling into a frequency range beyond that of mechanical vibrations, as a reference optical beam and a measurement optical beam;

passing the measurement optical beam through a blood-carrying body part to form a passed measurement optical beam;

measuring the reference optical beam and converting it into a electrical reference signal having a phase corresponding to the polarized-modulated optical beam, measuring the passed measurement optical beam and converting it into a electrical measurement signal having a phase corresponding to the passed measurement beam, preferably using a balanced receiver having means for dividing the passed measurement optical beam into a polarized component and a depolarized component, and determining a scattering-free probe electric signal having a phase from the balanced receiver;

determining a phase difference between the reference electric signal and the probe electric signal; and converting the phase difference into information relating to the concentration of glucose.

One such apparatus includes:

a laser beam source;

an optical phase modulator including a polarizer, an optic-fiber system that has an input coupler that couples the polarized laser beam into two polarization preserving fiber-optic conductors, a phase shifter that strains one of the fiber-optic conductors to modulate the beam propagating therein, an output optical coupler that recombines and coherently mixes the phase modulated beam and the unmodulated beam and then couples the combined beams into the outputs of the two fiber-optic conductors, a quarter-wave plate structure that converts the respective outputs of the two fiber-optic conductors into a polarized-modulated reference beam and a measurement beam;

a glucose measuring head that has an aperture to receive a blood-carrying tissue and a balanced receiver which receives the measurement optical beam after it passes through the tissue and produces an electrical measurement signal corresponding to the phase shift due to optical interaction with glucose in the blood; and an electronic signal processing unit that converts the phase difference between the balanced receiver output and the reference beam into a measurement of the glucose concentration.

The phase difference is preferably measured by subtracting the phase of reference electric signal from the phase of the scattering-free probe electric signal. The blood-carrying body part may be any well perfused tissue in which blood vessels are distributed with high density such as an appendage, e.g., finger, earlobe, toe or bridge of the nose. In the case of a measurement carried out with a finger, the laser beam is preferably transmitted through the nail-bed, which is especially concentrated with blood vessels.

BRIEF DESCRIPTION OF THE DRAWINGS

The above and other objects and advantages of the invention will be apparent upon consideration of the following detailed description taken in conjunction with the accompanying drawings, in which like reference characters refer to like parts throughout, optical signals are shown by double lines and electrical signals are shown by single lines, and in which:

FIG. 2 is a schematic structural view of the optical phase modulator of FIG. 1;

FIG. 3 is a perspective view of a section of the phase shifter of FIG. 2;

FIGS. 3a, 3b, and 3c are graphs illustrating the positions of axes of polarization with respect to an X-Y reference coordinate plane at three locations in the optical phase modulator of FIG. 2, namely at the optical polarizer output, in a first arm of the phase modulator, and in a second arm of the phase modulator, respectively;

DETAILED DESCRIPTION OF THE INVENTION

Figure 1:
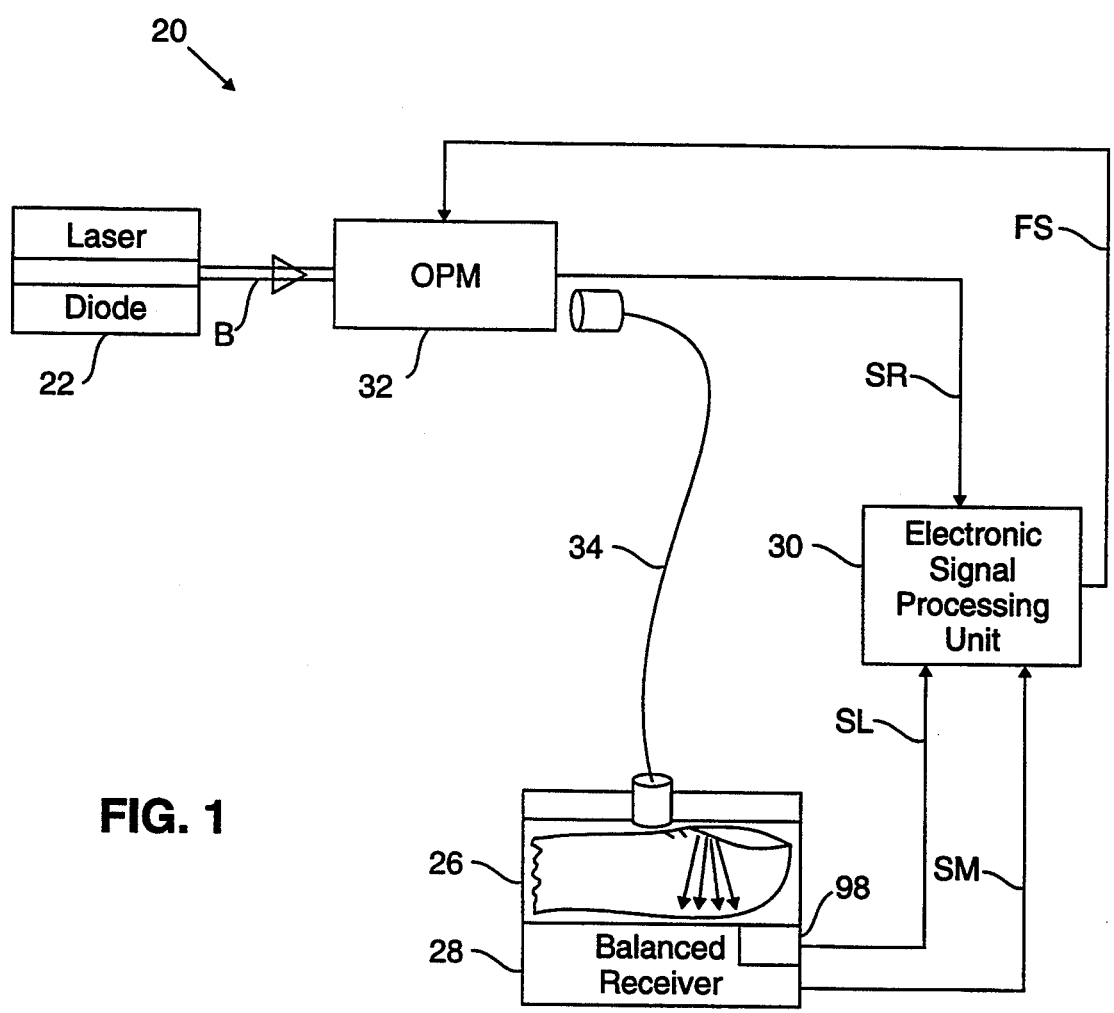
FIG. 1 is a block diagram of an apparatus in accordance with a preferred embodiment of the present invention.

A schematic block diagram of the apparatus of the invention is shown in FIG. 1. The apparatus, which is designated in general by reference numeral 20, includes a laser source 22 which produces a laser beam B, an optical phase modulator (OPM) 24 which receives laser beam B from laser source 22, a glucose measuring head 26 which contains a sensor in the form of a balanced receiver 28, and an electronic signal processing unit 30 connected to OPM 32 and to balanced receiver 28. Glucose measuring head 26 is connected to OPM 32 via a single-mode polarization-maintaining fiber-optic link 34.

Laser source 22 is preferably a laser diode which operates in the wavelength of 750 to 1000 nm (the near-infrared range), e.g., 850 nm, with a low-coherence length and preferably with a low-noise intensity and phase variation. A laser source of such type is produced, e.g., by Spectra Diode Labs, San Jose, Calif. Laser source 22 has a corresponding power-supply unit (not shown). It should be understood that other light sources and other wavelength ranges corresponding to other optical activity peaks for glucose (and similar peaks for other blood constituents) could be used.

The structure of OPM 32 is schematically shown in FIG. 2. Referring to FIGS. 2-5, OPM 32 comprises the following elements, arranged sequentially in the direction of propagation of laser beam B emanating from laser beam source 22: an optical isolator 36 which prevents back reflection of laser light to laser source 22, an input polarizer 38, two fiber-optic arms 40 and 42 which are interconnected by means of an input optical coupler 44 and an output optical coupler 46, an optical phase shifter 48 which is attached to fiber-optic arm 40, a quarter-wave plate 50, a glucose reference cartridge 52, an output polarizer 54, and a photodiode 56.

Optical polarizer 38 polarizes laser beam B so that the direction of its polarization forms a 45° angle to axis X, where, as shown in FIG. 3a, axis X is one of coordinate axes of the reference X-Y coordinate system. FIG. 3a is a graph illustrating position of the axis of polarization with respect to an X-Y reference coordinate plane at the output of polarizer 38.

Fiber-optic arms 40 and 42 are used to propagate light from laser source 22 to output quarter-wave plate 50. Each of fiber-optic arms 40 and 42 supports propagation of light in one of two orthogonally polarized modes. In particular, fiber-optic arm 40 is oriented so that it can support propagation of light mode with Y-axis direction of polarization, as illustrated in FIG. 3b, and fiber-optic arm 42 is oriented so that it can support propagation of light mode with X-axis direction, as illustrated in FIG. 3c.

At its end facing optical polarizer 38, fiber-optic arm 40 has an optical lens 58 which is known as a GRIN rod microlens. GRIN rod microlens 58 is a gradient index lens which has an index of refraction which varies in a predetermined relationship with the thickness of the lens. From GRIN rod microlens 58, the laser beam is coupled into arm 40 and passes to input optical coupler 44.

Input optical coupler 44 is formed by fusing fiber-optic arms 40 and 42. Commercial optical couplers are available, e.g., from SEASTAR Optics, Inc., Seattle, Wash. It is analogous in its action to a beam splitter with a 50:50 ratio, and splits laser beam B into two components B1 and B2. Beam component B1 propagates along fiber-optic arm 40 and beam component B2 propagates along fiber-optic arm 42. However, in as much as each arm supports a different one mode of propagation, the components B1 and B2 are not identical.

Referring to FIG. 3, phase shifter 48 is made in the form of a thin-walled piezoceramic ring 60 around which fiber-optic arm 40 is wrapped to form a coil 62. Commercial phase shifters of this type are available from, e.g., Burleigh Instruments, Inc., Burleigh Park, Fisher, N.Y. Piezoceramic ring 60 is electrically connected to electronic signal processing unit 30 (not shown). Unit 30 sends to piezoelectric ring 60 a signal FS, preferably an AC voltage which causes alternating contractions of piezoceramic ring 60, and thus phase modulates optical beam B1.

Figure 9:
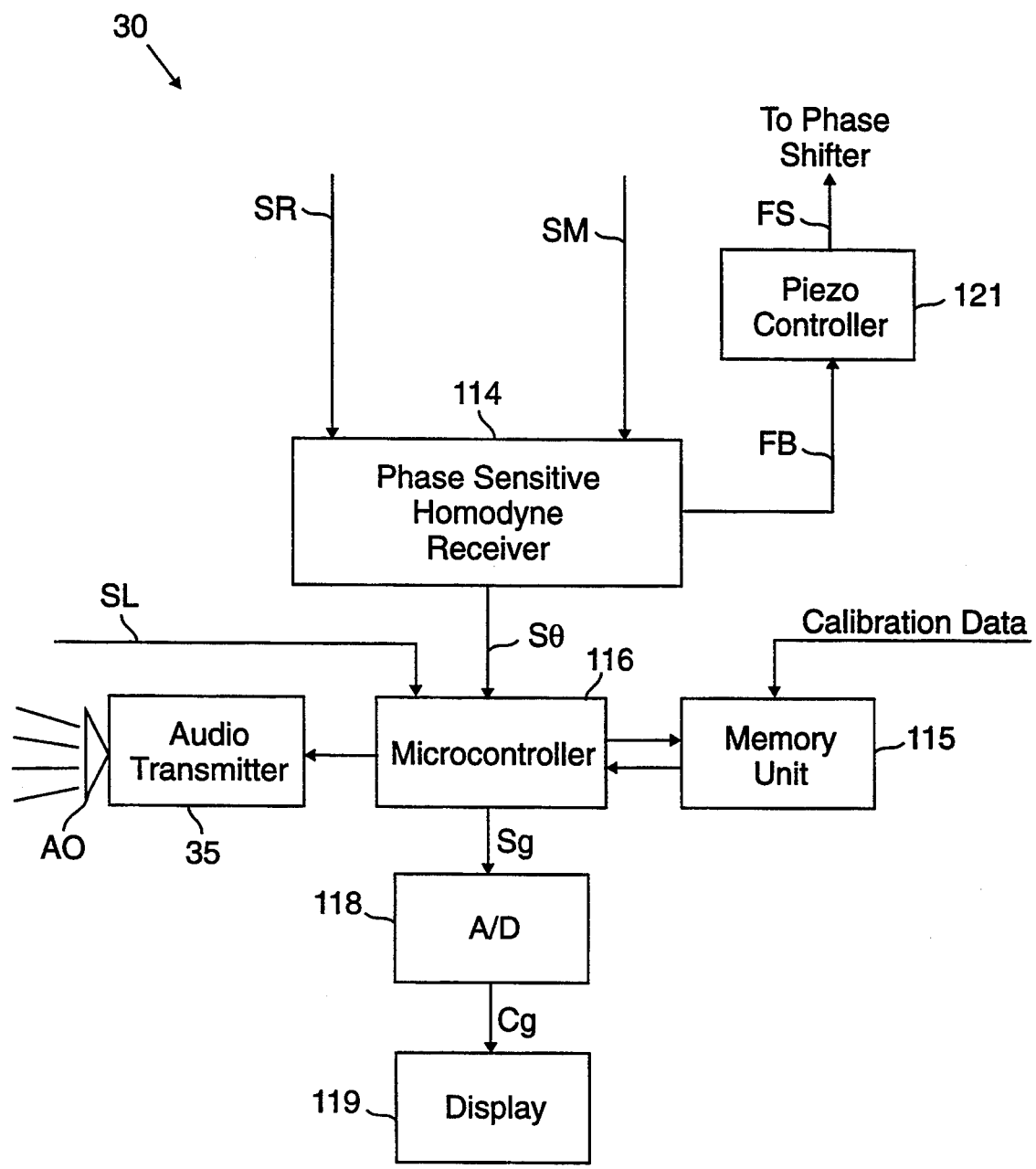
FIG. 9 is a block diagram of the electronic signal processing unit of FIG. 1.

Preferably, phase shifter 48 is controlled by a piezoelectric controller 121 (shown in FIG. 9). Piezoelectric controller 121 is a conventional circuit that generates a modulating signal FS, e.g., a sawtooth or triangular waveform at a selected frequency f, preferably responsive to a feedback control signal FB from electronic signal processing unit 30 (as described below), and causes ring 60 to vibrate accordingly.

Output optical coupler 46 also is formed by fusing optical fiber arms 40 and 42 to provide coherent mixing of the two light propagating modes of arms 40 and 42. As a result, each output portion 40a and 42a of a respective optical fiber arms 40 and 42 has a complementary coherent mixture of optical beams B1 and B2 with an orthogonal direction of polarization. Each output portion 40a and 42a is terminated in a GRIN rod microlens, lenses 43 and 45, respectively.

GRIN rod microlens 43 is aligned with quarter wave plate 50 window 50a and GRIN rod microlens 45 is aligned with quarter wave plate 50 window 50b. Quarter-wave plate 50 is a conventional device which introduces a phase delay equal to a quarter of the wavelength of the incident beam and is characterized by a fast axis and a slow axis. Quarter-wave plate 50 has a direction of its axis of polarization parallel to that of input polarizer 38. As a result, the beam emitted from GRIN rod microlens 43, after passing through window 50a, is a polarized-modulated optical beam which is used as a reference optical beam BR. Similarly, the beam emitted from GRIN rod microlens 45, after passing through window 50b, is a polarized-modulated optical beam which is used as a measurement optical beam BM. Reference optical beam BR is passed through a polarizer 54 and sensed by a photodetector 56 which produces an electrical reference signal SR corresponding to the phase of optical beam BR.

Figure 6:
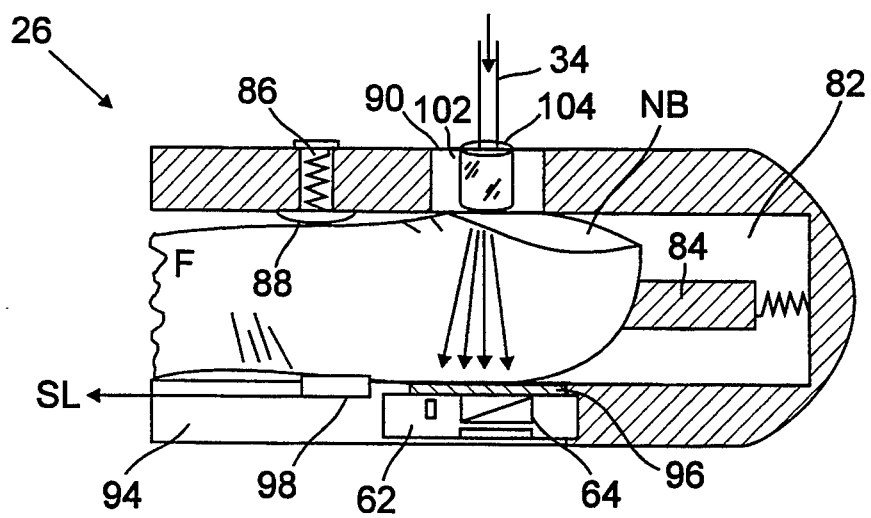
FIG. 6 is a schematic structural view of a remote glucose measuring head for measurement carried out on a finger in accordance with a first embodiment of FIG. 1.
Figure 7:
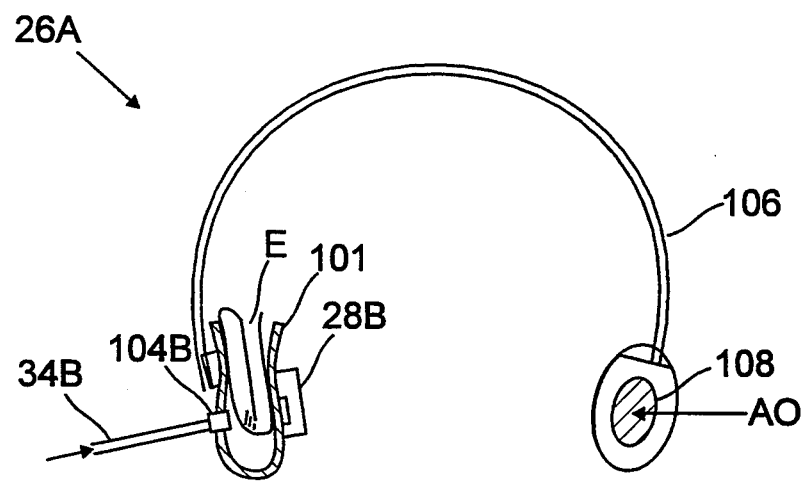
FIG. 7 is a schematic structural view of a remote glucose measuring head for measurements carried out on an earlobe in accordance with a second embodiment of FIG. 1.

Glucose measuring head 26, which receives the blood-carrying tissue to be measured, may be either securely attached to optical transducer 30 (not shown) or physically disconnected from optical transducer 30 for remote use and coupled to OPM 32 by an optical fiber link 34 (shown in FIGS. 1, 6, 7). It receives measurement optical beam BM and, as discussed below, produces an output electrical measurement signal SM corresponding to the phase of the measurement optical beam BM after is has passed through the tissue.

Electronic signal processing unit 30 is connected to OPM 32, receives electric signals SR, SM, and a signal SL corresponding to the thickness of the tissue through which the optical beam BM passes and provides a piezoceramic control signal FS. Unit 30 processes signals SR and SM and produces a measurement phase difference signal SΘ. The measurement signal phase difference $\Theta_M$ is then taken together with signal SL and calibration data (which provides information regarding the effective thickness of the blood-carrying body) and converted into information about the glucose concentration. The information may be displayed, e.g., in a decimal digital form on visual display 119, which is connected to electronic signal processing unit 30. Signal FS is used to provide a linear motion of piezoceramic ring 60 with a fixed frequency f and to avoid hysteresis.

Because in many cases people suffering from diabetes have poor vision, signal processing unit 30 also (or alternatively) may be connected to audio transmitter 35 having an audio output AO (see FIG. 6B). Audio transmitter 35 may repeat the glucose information in an audible form, e.g., by synthesized speech as is conventionally used in the telecommunications field.

Figure 4:
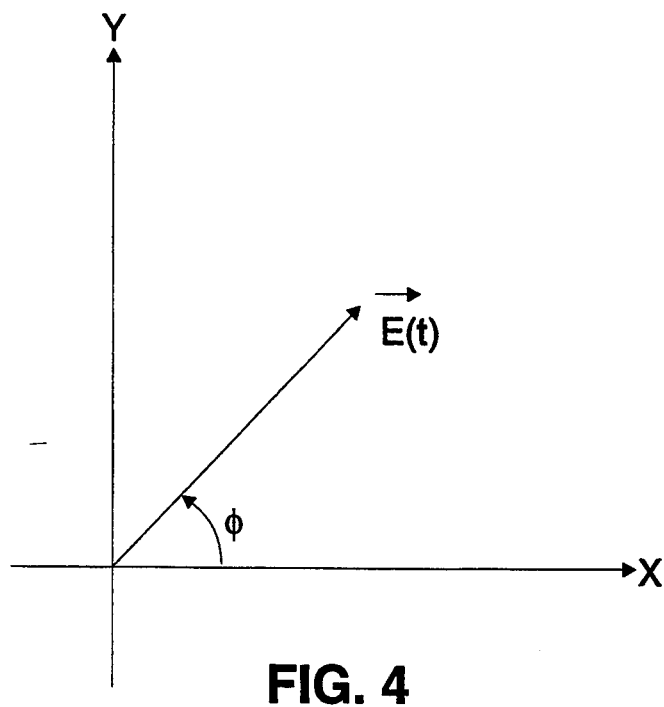
FIG. 4 is a graph illustrating the rotating vector representation of an output electric field of an optical phase modulator in the plane of travel.

Each output optical beam BR and BM is a polarized-modulated optical beam that is characterized by the strength of an electrical field E. As shown in FIG. 4, each above-mentioned field E can be represented by a coordinate system (axes X and Y) and a vector $\vec{E}$ of polarization which rotates in the plane XY with a frequency f/2. In this drawing, angle $\phi$ is an angle of rotation of vector $\vec{E}$ which varies with the above-mentioned frequency f/2. Angle $\phi$ is determined by the following formula:

$$\vec{E}(t) = \vec{E}_o e(t)$$

$$\vec{e}(t) = e, rar/\vec{e}/_x \cos \phi + \vec{e}_y \sin \phi$$

$$\phi(t) = \phi_0 + \pi ft$$

where $\phi_o$ is a constant phase shift caused by the difference in the path lengths between two fiber-optic arms 40 and 42, vector $\vec{e}(t)$ is a single vector of polarization, vectors $\vec{e}_x$ and $\vec{e}_y$ are single coordinate vectors which show the directions of the coordinate axes, and $E_o$ is an amplitude of laser beam B.

Referring to FIGS. 2, 5, 5a and 5b, a cartridge 52 is placed between quarterwave plate 50 and output polarizer 54 for calibration purposes. Cartridge 52 contains two reference cells 52a and 52b and a transparent window 61. Cell 52a contains a first concentration $C_1$ of a glucose solution and cell 52b contains a second concentration $C_2$ of a glucose solution. Each cell has an equal optical pathlength (i.e., the length through which optical beam BR passes), e.g., 1.0 cm. Window 61 has the same construction as cells 52a and 52b except that it is empty. Alternatively, window 61 may be an aperture.

Figure 5:
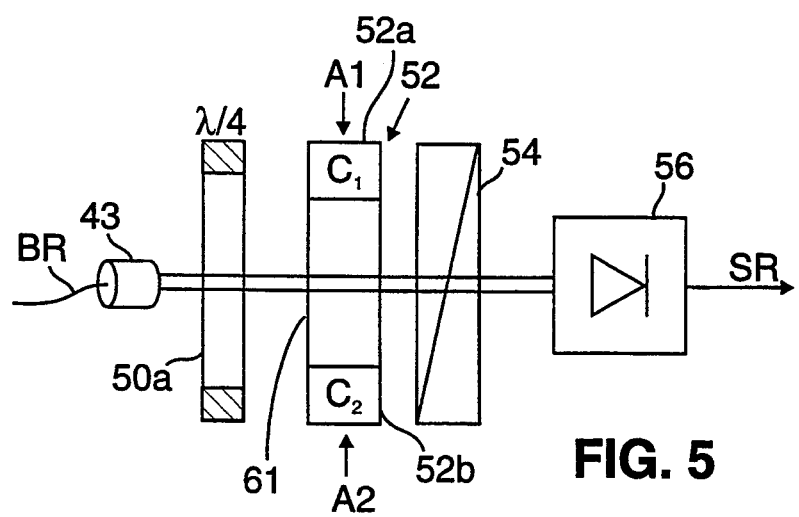
FIGS. 5, 5a, and 5b are partial structural views showing the different positions of the calibration cell cartridge of FIG. 2.
Figure 5A:
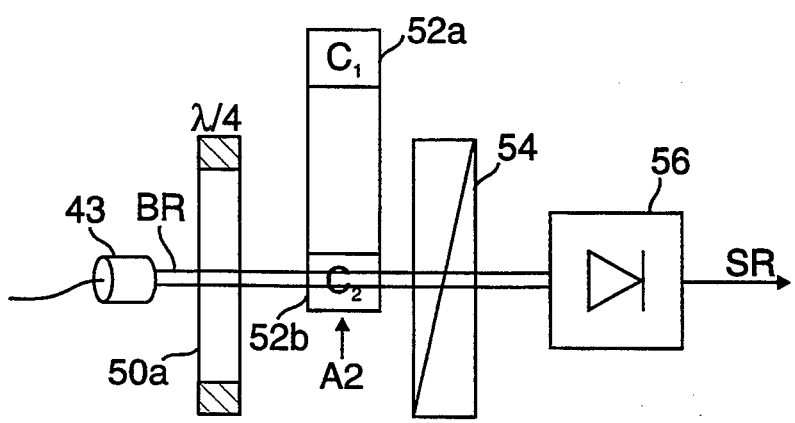
Figure 5B:
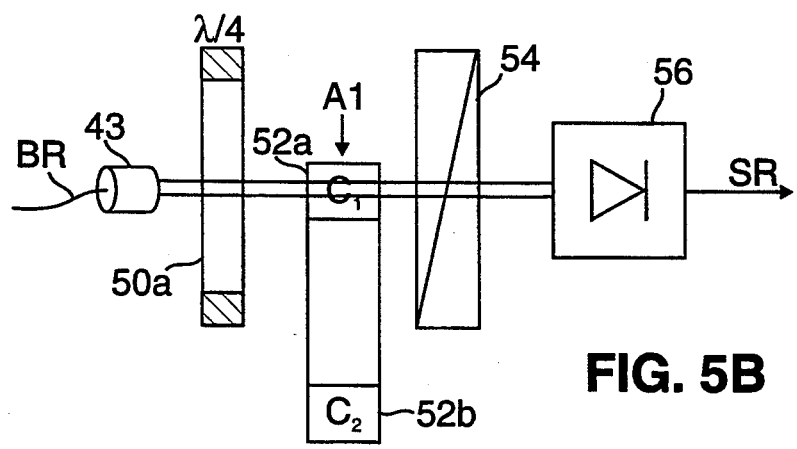

In this embodiment, cell 52a, transparent window 61, and cell 52b are linearly arranged on a sliding structure with window 61 located between cells 52a and 52b. Cartridge 52 may be shifted from the "central" position, illustrated in FIG. 5, in the direction of either arrow A1 or arrow A2 to the positions respectively shown in FIGS. 5A and 5B. The movement may be manual or automatic under control of a microcontroller 116 (shown in FIG. 9). In FIG. 5, cartridge 52 is in the central position and optical beam BR passes through window 61. This is the position used when measuring tissue. In FIG. 5A, cartridge 52 is shifted so that optical beam BR passes through cell 52a. In FIG. 5B, cartridge 52 is shifted so that optical beam BR passes through cell 52b. All three positions may be used for calibration purposes, as described below. It should be understood that other configurations for window 61 and cells 52a and 52b could be used, e.g., cells and window spaced about an axis so that cartridge 52 can be rotated from one position to the next.

Referring to FIGS. 2, 6, 7 and 8, the other optical beam, measurement optical beam BM, is passed through glucose measuring head 26 to balance receiver 28. Glucose measuring head 26 contains the object being measured, e.g., a blood carrying body part (tissue) such as a patient's finger F and produces a passed measurement optical beam, illustrated in FIG. 8 as beam BM1. Optical beam BM1 contains a polarized component which carries phase shift information related to the glucose concentration of the blood in the tissue through which it passed, and a depolarized scatter component which does not carry such glucose related information. More specifically, the transmission of measurement optical beam BM through blood-carrying body F changes the direction of polarization which is found in optical beam BM1. This introduces a phase shift $\Theta_M$ with respect to reference optical beam BR. Furthermore, the transmission of optical beam BM through body part (finger) F is accompanied by the depolarization of part of the incident optical beam BM, which is caused by the scattering of the optical beam in the tissue. The depolarized component of the passed optical beam BM1 has a time-constant average intensity and does not contain any information about the phase shift. Therefore, this component of the passed optical beam BM1 contributes only to the noise level of the signal. Typically, less than 5% of optical beam BM1 remains polarized (after passage through the blood-carrying body). However, because only the polarized component of optical beam BM1 produces an AC signal, that remaining 5% is sufficient data and may be used to recover the polarized signal.

Referring to FIG. 6, one embodiment of the structure of glucose measuring head 26, in which an object, such as finger F, is inserted into an object-receiving recess, is shown. This unit 26 has a housing 80 which has a central opening 82, a spring-loaded axial stop element 84, and a side opening 86 with a spring-loaded pressure element 88. Central opening 82 serves to receive a finger F as a measuring object. Housing 80 also has a second side opening 90. Opening 90 serves for directing optical beam BM onto a nail bed NB of finger F. Axial stop element 84 serves to adjust the position of finger F so that beam BM intersects nail bed NB. Pressure element 88 is intended for the fixation of finger F during measurement and for increasing the amount of blood in the measured portion of finger F. An increase in the amount of blood in the measured portion of finger F reduces the scattering of the light transmitted through finger F and increases the signal-to-noise ratio of the measurement.

In this embodiment, glucose measuring head 26 is connected to window 50b of quarter-waveplate 50 by a polarization-maintaining fiber-optical link 34. A ferrule 102 is inserted into side opening 90 and supports a GRIN rod microlens 104 for coupling polarized light beam BM from fiber 34 into unit 26. GRIN lens 104 is intended to produce an output optical beam BP in a collimated form at the output of optical fiber 34. This is used because optical beam BM loses its collimation properties when it is transmitted through optical fiber 34. Polarization preserving optical fibers and GRIN rod micro-lenses are commercially available products.

On the side of finger F opposite to nail bed NB of finger F, housing 80 has a recess 94 accommodating balance receiver 28 which is described in detail later. A beam-splitter plate 64 of balance receiver 28 is located on the side of finger F opposite to nail bed NB, i.e., on the side of digital pulp DP of finger F. Beam-splitter plate 64 is protected by a glass plate 96.

Recess 94 also contains a sensor 98 which determines the thickness of finger F in the portion being measured. Sensor 98 generates a signal SL which is directed to signal processing unit 116. Sensor 98 may be a capacity-type or a resistor-type sensor that is capable of determining variations in the capacity or in the resistance between the conditions as they are in the absence of finger F and once finger F has been inserted.

Referring to FIG. 7, another embodiment of glucose measuring head 26B, which is intended for using a patient's earlobe E as a blood-carrying body, is shown. In this embodiment, glucose measuring head 26B is attached to an arc-shaped head appliance 106 such as an arc shaped head holder or band or headband of the same type as the one used in conventional headsets, including those having earphones for supporting microphones on the head of a wearer.

Head appliance 106 supports a speaker/microphone 108 for reproducing audio information about the glucose concentration, which is provided by suitable circuitry (not shown) which is supplied from audio output AO of an audio transmitter 35. See FIG. 9. Preferably, speaker/microphone 108 is supported at one end of head appliance 106. Head appliance 106 also supports a U-shaped clip 101 which, in turn, supports glucose measuring head 26a and which can be attached to earlobe E of the patient. One side of clip 101 holds a GRIN rod lens 104b with an optical fiber link 34b while the other side of clip 101 holds a balance receiver 28b with a thickness sensor (not shown). Structurally, GRIN rod lens 104b, balance receiver 28b, and the sensor of the embodiment of FIG. 7 may be the same as those of FIG. 6.

Figure 8:
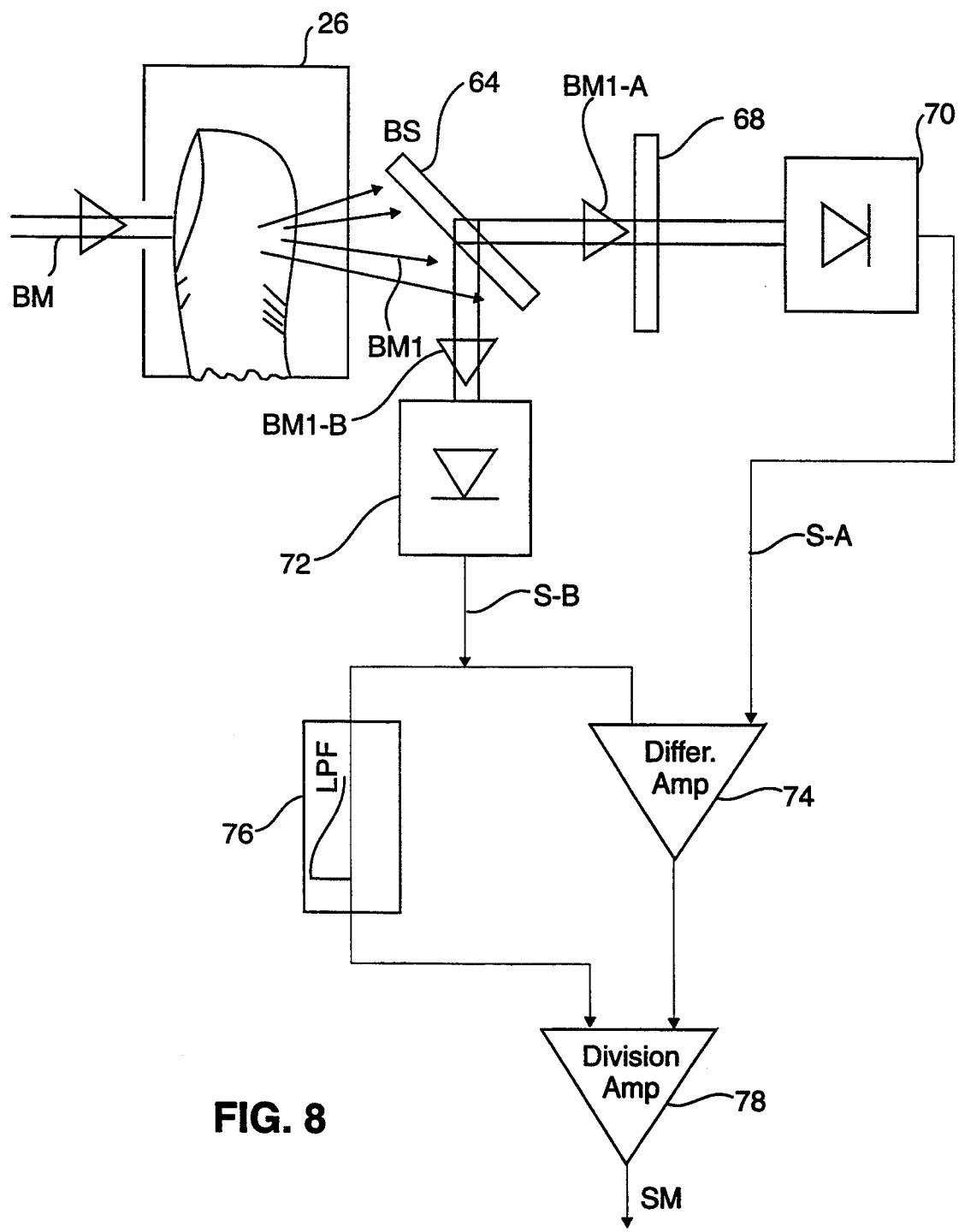
FIG. 8 is a block diagram of the balanced receiver of FIG. 1.

Referring to FIG. 8, balanced receiver 28 functions to subtract out electronically the depolarized portion of the optical signal BM1 and to leave only the polarized component. It has as its output an electrical measurement signal SM corresponding to the polarized component of passed measurement optical beam BM1.

The structure of balanced receiver 28 in accordance with a preferred embodiment of the invention is shown in FIG. 8. Receiver 28 includes a beam-splitter plate 64 with a 50:50 splitting ratio. Beam splitter plate 64 receives passed measurement optical beam BM1 and divides optical beam BM1 into two equal components BM1-A and BM1-B. One of these components is converted into a polarized component. In this regard, located on the path of optical beam component BM1-A are a polarizer 68 and a photodetector 70. The other component is used as a depolarized component. In this regard, located on the path of optical beam BM1-B is a photodetector 72. Photodetectors 70 and 72 are preferably identical and matched and produce polarized component electric signal S-A and depolarized component electric signal S-B on their respective outputs. Electrical signal S-A also is referred to as the polarized electric component. Electric signal S-B also is referred to as the depolarized electric component.

Balanced receiver 28 also includes a difference amplifier 74, a low-pass filter 76, and a division amplifier 78. Output electric signals S-A and S-B of photodetectors 70 and 72 are directed to the inputs of difference amplifier 74. The output of difference amplifier 74 is connected to an input of division amplifier 78. Low-pass filter 76 is located between photodetector 72 and division amplifier 78 and passes the DC signal components of signal S-B. The other input to division amplifier 78 is the low pass filtered output of photodetector 72. The signal SM output of division amplifier 78 is the ratio of its inputs and provides electrical measurement signal SM.

Referring to FIG. 9, electronic signal processing unit 30 includes a phase-sensitive homodyne receiver 114, which receives the reference electric signal SR and the measurement electric signal SM and produces on its output an electric signal S$\Theta$ which is proportional to a blood glucose concentration, a microcontroller 116, which processes signal S$\Theta$ in order to convert it into a glucose-concentration signal $S_G$, and an analog-digital (A/D) converter 118 which receives, e.g., signal $S_G$ and converts it into digital information $C_G$. The output of A/D converter 118 is passed to display 119 for displaying the obtained information about the concentration of glucose in the blood.

Phase-sensitive homodyne receiver 114 is a device which determines the phase difference between signals SR and SM. It may operate based on either a lock-in amplifier technique or a time-interval counter operating in a phase mode, in accordance with conventional techniques. One useful phase-sensitive homodyne receiver, with a resolution of 0.001° in phase difference, is available from Stanford Research Systems, Inc., Sunnyvale, Calif.

Electronic signal processing unit 30 also contains a piezocontroller 121 which is connected via a feedback signal FB with phase-sensitive homodyne receiver 114. Piezocontroller 121, in turn, is connected to phase shifter 48 (FIG. 2). Piezocontroller 121 is a device which controls waveforms of an AC voltage signal FS supplied to phase shifter 48.

Electronic signal processing unit 34 also contains a memory unit 115 which is connected to microcontroller 116 and which may store data required for custom calibration of apparatus 20, patient's measurement data, etc.

In order to exclude the effect of statical phase shift $\Theta_o$, which may occur because of temperature (ambient or sample) variations, misalignment in the optical system, imperfect optics (designed not exactly for the given wavelength), etc., each measurement procedure preferably begins with calibration of apparatus 20. For this purpose, prior to actual measurement on the object, a reference calibration procedure is carried out by first passing optical beam BR through transparent window 61 (FIG. 5) and then sequentially through cells 52a and 52b. Ideally, the calibration procedure using cells 52a and 52b can be omitted. However, for manufacturability and use over long periods of time, e.g., months and years, frequent calibration is desired for continued accuracy.

For the calibration, cells 52a and 52b are sequentially shifted (in any order) into the positions shown in FIGS. 5A and 5B in which they alternatively interfere with the optical path of optical beam BR. The calibration procedure is the same as measuring the glucose concentration in tissue F, except that no tissue is inserted in glucose measuring head 26, the meanings of signals SR and SM are reversed, and signal SL is not used because the sample cell path length of cartridge 52 is known, i.e., 1 cm. The details of the propagation of the optical beams and processing of the obtained information is discussed below with reference to the measurement of glucose in blood carrying body part F.

Figure 10:
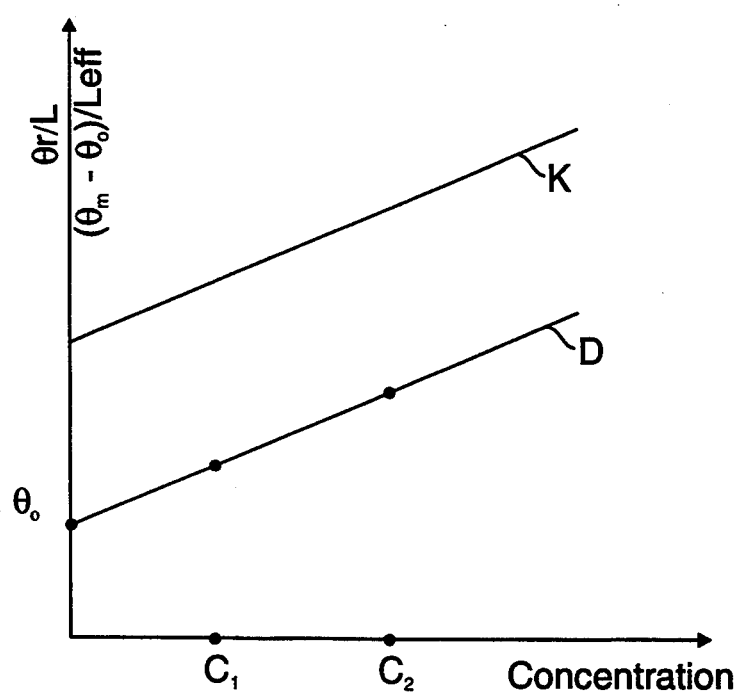
FIG. 10 is a graph illustrating a calibration procedure.

Both cells 52a and 52b contain glucose solution samples of different known glucose concentrations $C_1$ and $C_2$. The results of the calibration measurement will thus produce two points in a relationship between a reference phase difference $\Theta_R$ (per 1 cm of the pathlength) and glucose concentration $C_G$. This is shown in FIG. 10. The results of the calibration are shown by the curve labelled D in FIG. 10. From this reference calibration, one can obtain statical phase shift $\Theta_o$ per 1 cm of pathlength. It should be understood that cells 52a and 52b alternatively may contain or comprise some optically active material (in any state), other than two different solutions of glucose, which have the same effects on the polarized-modulated laser beam as do the glucose solutions at two different known concentrations, but have a longer useful life than solutions of glucose.

In measuring tissue however, the phase shift $\Theta_M$ between electrical measurement signal SM and electrical reference signal SR will depend on many factors, including effective pathlength $L_{EFF}$ for beam BM. Effective length $L_{EFF}$ is only that part of the optical path of beam BM which is passed only through the blood-filled portion of the measurement object and differs from actual thickness of the finger. Therefore, in order to obtain the glucose-concentration information from the results of measurement, it is necessary to subtract all extraneous data.

Phase shift $\eta_M$ may be generally expressed by the following formula (1):

$$\Theta_M = \alpha_{GL} C_{GL} L_{EFF} + \Theta_{SUB} + \Theta_o \quad (1)$$

where $\Theta_{SUB}$ is a phase shift introduced by other blood components which also are optically active, i.e., subject to optical rotation at the wavelength of light used, and $\alpha_{GL}$ is a known optical parameter which, for a given wavelength, may be obtained from spectroscopy data.

Each subject, however, has $\Theta_{SUB}$ which is constant in time and does not depend on the changes in the glucose concentration. This parameter and effective path-length $L_{EFF}$ may be obtained based on two (or more) measurements taken at different glucose concentrations for which the glucose concentrations are obtained by a conventional invasive procedure (e.g., a finger poke measurement, laboratory analysis, or other biochemical analysis method, preferably on the basis of finger poke measurements). For this purpose, the concentration of glucose is measured at least twice: for example, once on an empty stomach and once an hour after administration of a concentrated solution of dextrose (or any other substance which raises the blood glucose level). These calibrating measurements need be performed only once for each person, prior to using the apparatus for the first time, as part of a start-up calibration procedure. The results of such two calibrating measurements may be expressed by the following formulae (2.1) and (2.2):

$$\Theta_{M1} = \alpha_{GL} C_{GL1} L_{EFF} + \Theta_{SUB} + \Theta_o \quad (2.1)$$

$$\Theta_{M2} = \alpha_{GL} C_{GL2} L_{EFF} + \Theta_{SUB} + \Theta_o \quad (2.2)$$

where $C_{GL1}$ and $C_{GL2}$ are the measured concentrations of glucose and $\Theta_{M1}$ and $\Theta_{M2}$ are the phase shifts measured by apparatus 20 at approximately the same time that the two glucose samples are obtained, respectively. These values are introduced into and stored in memory unit 115. The more calibration measurements that are made during the one-time start-up calibration procedure, the more accurate the calibration information will be.

From formulae (2.1) and (2.2), effective length $L_{EFF}$ can be expressed as follows:

$$L_{EFF} = \frac{\Theta_{M2} - \Theta_{M1}}{\alpha_{GL}(C_{GL2} - C_{GL1})} \quad (3)$$

Substituting formulas (3) into (1), a general expression for $\Theta_M$ is obtained as follows:

$$\Theta_M = \frac{C_{GL}(\Theta_{M2} - \Theta_{M1})}{(C_{GL2} - C_{GL1})} + \Theta_{SUB} + \Theta_o \quad (4)$$

Now the curve corresponding to formula (4) should be compared with reference calibration curve D. In order to ensure meaningful comparison, both curves must be normalized against the pathlength, i.e., each curve is divided by its pathlength.

FIG. 10 shows the normalized curve D and curve K. For curve D, the ordinate represents $\Theta_R/L$ (L=1 cm). For curve K, the ordinate represents $(\Theta_M - \Theta_o)/L_{EFF}$. Theoretically, both curves are parallel and represented by straight lines. In reality, however, they may have some deviations from the theoretical condition. Accordingly, memory unit 115 contains a suitable algorithm, which can be derived from experimentally acquired data, for processing the above-mentioned data by known methods of correlation analysis so as to minimize the above-mentioned deviations. One of the variables of such algorithm may be an actual thickness of the finger. It is understood that the above formulae are parts of the algorithm and that all calculations are performed automatically in microcontroller 116. Upon completion of the calibration procedures, including the one-time start-up calibration, apparatus 20 is ready for actual measurement.

Operation of apparatus 20 of the invention for measuring the blood-glucose concentration will be now described for the case of glucose measuring head 26 built into the apparatus (i.e., for non-remote version).

When an apparatus 20 is switched on, laser diode 22 generates a laser beam B which is directed to fiber-optic arm 40. When beam B passes through input optical coupler 44, it is split into two mutually-orthogonal beam components B1 and B2. One of them, i.e., beam component B1, which propagates through arm 40, is subjected to phase modulation under the action of phase shifter 48. The other, i.e., beam component B2, which propagates through arm 42, remains unchanged. In output coupler 46 both beam components B1 and B2 are coherently mixed. As a result, after passing through output optical coupler 46, each output portion 40a and 42a of respective optical fiber arm 40 and 42 has a complementary coherent mixture of optical beams B1 and B2 with an orthogonal direction of polarization. These beams then pass through windows 50a and 50b of a quarter-wave plate 50 and are transformed into linear-polarized waves, respectively to form optical beams BR and BM. As shown in FIG. 4, the direction of polarization of these waves rotates with the frequency corresponding to that of phase shifter 48.

Measurement optical beam BM is sent directly to glucose measuring head 26. Reference optical beam BR is sent to reference photodetector 56 via cell cartridge 52 and polarizer 54. Reference photodetector 56 produces a reference electrical signal SR.

With reference to FIG. 6, for measuring the blood glucose level, the patient inserts his/her finger F into opening 82 against spring-loaded stop element 84 and adjusts the position of finger F so that nail bed NB is aligned with the position of side opening 90. At the same time, spring-loaded pressure element 88 applies a pressure to finger F behind the measurement portion, whereby the amount of blood in the finger flesh to be measured is increased to increase the sensitivity of measurements.

Measuring beam BM passes through the blood of finger F and becomes passed measurement beam BM1. Transmission of measuring beam BM through finger F changes the direction of polarization of the beam because glucose is an optically active material for the wavelength of measurement optical beam BM. This introduces a phase shift $\Theta_M$ for optical beam BM1 with respect to reference optical beam BR. For a wavelength $\lambda = 850$ nm and a blood glucose concentration of 70 mg/100 ml, the phase shift is on the order of 4.7 millidegrees.

The transmitted beam BM1 passes through protective plate 96 to a beam-splitting plate 64 of balanced receiver 28. In balanced receiver 28, beam BM1 is split into two beams BM1-A and BM1-B. Component BM1-A of the beam is directed through polarizer 68 to photodetector 70. Photodetector 70 produces an electrical signal S-A, corresponding to the polarized component of beam BM1-A which is input to difference amplifier 74. At the same time, component BM1-B of beam BM1 is directed to photodetector 72 which produces an electric signal S-B corresponding to the non-polarized (or depolarized) component of beam BM1. Signal S-B also is input to difference amplifier 74.

Difference amplifier 74 then provides an output that is the difference between the electrical signals S-A and S-B corresponding to depolarized and polarized components of optical beams BM1-A and BM1-B. The output signal of difference amplifier 74 thus carries information only about the polarized component BM1-A. However, the amplitude of this difference signal still contains noise associated with light scattering. To further reduce this noise component, the amplitude of the output signal from difference amplifier 74 is divided, in division amplifier 78, by the amplitude of the signal from photodetector 72 which contains the same scattering noise. More specifically, the output of photodetector 72 is passed through low-pass filter 76 for removing frequencies above 10 to 100 Hz and the filtered signal is provided as the denominator to the division amplifier 78. The resulting measuring electric signal SM thus carries information about polarized component BM1-A, but the amplitude of signal SM is free of the noise influence.

Reference electric signal SR and measuring electric signal SM are then passed to phase-sensitive homodyne receiver 114. An output of homodyne receiver 114 is provided as a feedback signal FB to piezoelectric controller 121. Receiver 114 extracts a phase-difference signal $S\Theta$, which is sent to the input of microcontroller 116. At the same time, microcontroller 116 receives length measurement signal SL from sensor 98 and calibration data from memory unit 115.

On the basis of the algorithm, phase difference signal $S\Theta$, length signal SL, and calibration data, microcontroller 116 produces a signal $S_G$ proportional to the concentration of glucose. Signal $S_G$ is converted by A/D converter 118 into a digital glucose concentration information $C_G$ which can be shown and/or indicated on display 119. The apparatus uses averaging techniques for the measurements to extract the best signal to noise information and may require up to several seconds to produce a glucose concentration measurement. Averaging will average out variations in blood volume due to pulsatile blood flow, motion artifact and other movements.

Apparatus 20 made in accordance with the embodiment of a remotely located glucose measuring head shown in FIG. 6 operates in the same manner as the apparatus of the embodiment of FIG. 6 except that optical beam BM is transmitted to finger F (or another blood-carrying part), via optical-fiber link 34 and GRIN lenses 104 and 104A.

Referring to FIG. 7, in the case of apparatus 20 made in accordance with the embodiment of glucose measuring unit 26a, head appliance 106 is put on the patient's head as in the case of a conventional headset so that transducer 108 is located near one ear of the wearer while the lobule E of the other ear of the patient is clamped by clip 101. In this manner, ear lobule E is located on the optical path of optical beam BM between fiber-optical link 34b and balanced receiver 28b. All other parts operate on the same principle as similar parts of the previous embodiment.

In an actual construction, apparatus 20 may have small dimensions of about 40 cm × 15 cm × 20 cm, or less. This allows the use of the apparatus as a home and portable monitoring device. Use of customizable ASIC devices and/or customized integrated circuits will permit reducing the size further. A rechargeable battery (or replaceable battery) may be used to operate the system electronics to permit portable use.

Thus, it has been shown that the invention provides methods and apparatus for non-invasive precision phase-sensitive measurement of blood glucose. These methods and apparatus do not involve the use of mechanically moving parts, result in low-noise measurements, operate in the frequency range beyond that of mechanical vibrations, are suitable for use at home or as a portable blood monitoring device, utilize processing electronics which allow glucose-level measurements through high-scattering tissue, and are not restricted for use with an eye but applicable to other blood-carrying body parts. Advantageously also, the device and methods use a single near infrared light source, e.g., a single laser diode. In addition, the device obtains a measurement from perfused blood-carrying tissue in effective real time, rather than from aqueous eye humor in which changes in the glucose concentration may lag behind the blood glucose concentration by two hours.

Although the apparatus and the method have been shown and described in the form of specific embodiments, these embodiments, their parts, materials, and configurations have been given only as examples, and many other modifications of apparatus and method possible. For example, the thin walled piezoceramic body 60 may have configurations other than a ring and can be made, e.g., as a strip to which the optic-fiber arm 40 may be attached. Cartridge 52 may be removable, stored separately, and inserted when necessary, rather than be incorporated into apparatus 20. An LED (light-emitting diode) operating in a near-infrared region of the spectrum with adequate collimating lenses may be used instead of a laser diode. Apparatus 20 also may be equipped with memory 115 of sufficient capacity for storing a log of the patient's measurements, e.g., date, time and values. It also may be equipped for storing information regarding medication dosages administered, e.g., units of insulin, using a suitable keypad or other data entry system. In the case that apparatus 20 is constructed for use as a hospital or clinic-based unit, it may contain more substantial computing functions such as calibration data for each patient it will service, maintain a log of each patient's measurements and also may include additional electronic circuitry for improving the accuracy of measurements. For example, a feedback signal may be sent to the laser source to stabilize amplitude and phase noise variation of the laser beam.

The present invention is particularly useful for monitoring blood constituents which undergo short term changes, such as glucose, in the presence of other optically active blood or tissue constituents (whether less dominant than, e.g., glucose), e.g., protein, which either do not change or change very slowly with time. In the case where the other optically active components do change somewhat with time, short term and long term averaging techniques may be used to control the effects of a change in the other optically active components. Similarly, tile start-up calibration using two or more invasive glucose measurements could be infrequently used, e.g., once a year or when the patient's weight has changed significantly.

The invention also may be useful for identifying the concentration of an optically active substance that is added to blood and selectively bonds to a desired blood constituent. For example, substances such as optically active monoclonal antibodies that bind to specific antigenic determinants of a selected blood constituent or cell subpopulation may be used. This provides for indirectly measuring non-invasively blood components that are not significantly or sufficiently optically active for diagnostic and therapeutic purposes.

One skilled in the art will appreciate that the present invention can be practiced by other than the described embodiments, which are presented for purposes of illustration and not of limitation.

I claim:

1. A method for determining non-invasively the concentration of glucose in a blood-carrying body part of a patient comprising the steps of:
   (a) splitting a laser beam into two polarized components and phase modulating one of the components with a modulation frequency above a range of mechanical vibrations and a phase, thereby providing a modulated component and an unmodulated component;
   (b) combining the modulated and unmodulated components and forming therefrom a reference optical beam and a measurement optical beam, each of which is a polarized-modulated laser beam;
   (c) passing the reference optical beam through a polarizer, sensing the polarized reference optical beam with a photodetector, and producing an electrical reference signal corresponding to the phase of the polarized-modulated optical beam;
   (d) passing the measurement optical beam through a blood carrying body part having glucose to be measured and a thickness to provide a passed measurement optical beam having a phase and
      (i) splitting the passed measurement optical beam into a polarized component and a depolarized component;
      (ii) converting the depolarized component into a depolarized component electric signal;
      (iii) converting the polarized component into a polarized component electric signal;
      (iv) subtracting the depolarized component electric signal from the polarized component electric signal to provide a first subtracted signal;
      (v) low-pass filtering the depolarized component electric signal to provide a low-pass filtered signal; and
      (vi) dividing the first subtracted signal by the lowpass filtered signal, thereby providing an electrical measurement signal corresponding to the phase of the passed measurement optical beam;
   (e) determining a phase difference between the electrical reference and measurement signals; and
   (f) determining the concentration of the glucose in the blood carrying body part illuminated by the measurement optical beam based on the determined phase difference.

2. The method of claim 1 in which step (a) further comprises:
   providing an optical phase modulator by joining together two lengths of polarization preserving fiber-optic conductors so that each fiber-optic length has an input end and an output end, providing an input optical coupler for coupling light received at each fiber-optic input end into both fiber-optic conductors, and providing an optical coupler output for mixing the light propagating in each fiber-optic and coupling said mixture to each fiber-optic output end;
   passing the laser beam through a polarizing element and into one of the fiber-optic conductors so that a polarized optical beam component propagates in each fiber-optic conductor with a different direction of polarization; and
   imparting the phase modulation to one of the two propagating polarized beam components to produce said modulated component and wherein the other propagating polarized beam component is the unmodulated component; and
   in which step (b) further comprises:
   combining coherently the modulated and unmodulated laser beam components at the output coupler and providing each fiber-optic conductor output with a complementary coherent mixture of the modulated and unmodulated beam components with an orthoganol direction of polarization; and
   passing the outputs of the first and second fiber-optic conductors through respective quarter-wave plate windows, thereby providing the polarized-modulated reference and measurement optical beams.

3. The method of claim 2 wherein the step of imparting a phase modulation further comprises attaching a piezoelectric body to one fiber-optic conductor between the input and output optical couplers, and activating the piezoelectric body to vibrate at the modulation frequency to deform the optical fiber to impart a phase modulation to the laser beam component propagating therein.

4. The method of claim 3 wherein the step of attaching includes attaching a thin-walled piezoceramic ring around which the one fiber-optic conductor is wound.

5. The method of claim 4 wherein the laser beam is a near infrared wavelength selected in the range of from 750 to 1000 mm, and the modulation frequency is selected in the range of from 650 Hz to 15,000 Hz.

6. The method of claim 3 in which step (d) further comprises providing a balanced receiver and performing steps d(i)–d(iii) using said balanced receiver.

7. The method of claim 6 in which step (e) further comprises processing the electrical reference and measurement signals using a phase sensitive homodyne receiver for producing therefrom a phase difference signal.

8. The method of claim 7 wherein step (e) further comprises feeding back a portion of the electrical reference signal for controlling the piezoelectric body.

9. The method of claim 7 in which step (f) further comprises:
   receiving information for calibrating the determined phase difference signal to the concentration of blood glucose in the blood carrying tissue;
   receiving the determined phase difference signal from step (e); and
   determining the concentration of the blood glucose based upon the determined phase difference signal and the calibration information.

10. The method of claim 9 further comprising obtaining the calibration information based on a first determined phase difference signal for a first known glucose concentration and a second determined phase difference signal for a second known glucose concentration and a predetermined linear relationship between the said-first and second phase difference signals and known glucose concentrations.

11. The method of claim 1, in which step (b) further comprises:

calibrating the reference and measurement electrical signals before performing step (d), the calibrating step further comprising:

selecting one of the measurement and reference optical beams as the calibrating optical beam;

passing the calibrating optical beam through a first cell of known thickness containing a solution corresponding to a first known concentration of glucose and determining a first data point corresponding to a measured phase difference for the first known concentration;

passing the calibration optical beam through a second cell of known thickness containing a solution corresponding to a second known concentration of glucose different from the first concentration and determining a second data point corresponding to a measured phase difference for the second known concentration; and determining calibration data based on the first and second data points to calibrate a determined phase difference for the blood glucose to be measured in step (d).

12. The method of claim 11, in which selecting the calibrating optical beam further comprises selecting the reference optical beam and further comprises:

providing a movable cartridge containing the first cell and the second cell; and moving the cartridge to present separately each of the first cell and the second cell to the reference optical beam and separately converting the transmitted optical beam through the first and second cells to first and second electrical measurement signals for determining the first and second data points; and presenting neither of the first and second cells to the reference optical beam for measuring blood glucose in step (d).

13. The method of claim 12, further comprising, prior to each measurement performing the calibration prior to step (d).

14. The method of claim 13, in which each polarized-modulated laser beam is a near infrared wavelength laser beam in the range of 750 to 1000 nm.

15. The method of claim 1, further comprising measuring the path length of the measurement optical beam through the blood carrying body part thickness.

16. The method of claim 15, in which the splitting step (d)(i) further comprises splitting the measurement optical beam using a beam splitter into a first transmitted measurement optical beam and a second transmitted measurement optical beam, providing the first transmitted measurement optical beam as the depolarized component, passing the second transmitted probe optical beam through a polarizer and providing the polarized second transmitted optical beam as the polarized component.

17. The method of claim 16, in which each polarized-modulated laser beam is a near infrared wavelength laser beam in the range of 750 to 1000 nm.

18. The method of claim 1 in which step (e) further comprises providing a phase sensitive homodyne receiver for receiving the reference and measurement electric signals and producing therefrom a phase difference signal.

19. The method of claim 1 in which step (f) further comprises:

receiving calibration information corresponding to a first and second determined phase difference signals based on two known concentrations of glucose and a predetermined relationship between the said two phase difference signals and said two known concentrations;

receiving the determined phase difference signal from step (e); and determining the concentration of the glucose in the blood carrying body part based upon the determined phase difference signal and the calibration information.

20. The method of claim 1 wherein the modulation frequency is selected from between 650 Hz and 10 KHz.

21. The method of claim 1 further comprising:

(g) measuring the thickness of the blood carrying body part being illuminated by the measurement optical beam and providing a length signal corresponding to the measured thickness;

wherein step (f) further comprises determining the glucose concentration based on the determined phase difference and the measured length signal.

22. The method of claim 1 in which step (f) further comprises:

receiving information for calibrating the determined phase difference signal to the concentration of blood glucose in the blood carrying tissue;

receiving the determined phase difference signal from step (e); and determining the concentration of the blood glucose based upon the determined phase difference signal and the calibration information.

23. The method of claim 1 in which step (f) further comprises:

measuring the thickness of the blood carrying tissue being illuminated by the probe optical beam as a length signal;

receiving information for calibrating the determined phase difference signal to the concentration of blood glucose in the blood carrying body part;

receiving the determined phase difference signal from step (e); and determining the concentration of the blood glucose based upon the determined phase difference signal, the calibration information, and the length signal.

24. The method of claim 23 further comprising obtaining the calibration information based on a first determined phase difference signal for a first known glucose concentration and a second determined phase difference signal for a second known glucose concentration and a predetermined linear relationship between the said first and second phase difference signals and the said first and second known glucose concentrations.

25. The method of claim 1 further comprising, prior to passing the measurement optical beam through the blood carrying body part to measure blood glucose concentration non-invasively, conducting a start-up calibration procedure and a reference calibration procedure, the start-up calibration procedure comprising the steps of:

(i) following steps (a)–(f) using a selected blood carrying body part having a first blood glucose concentration to determine a first measured phase difference and measuring the first blood glucose concentration invasively;

(ii) repeating steps (a)–(f) at least once using the selected blood carrying body part having a different blood glucose concentration, thereby determining a measured phase difference for an invasively measured different blood glucose concentration;

(iii) determining an effective thickness for the selected blood carrying tissue based on the phase differences determined in steps (i) and (ii);

(iv) determining a measurement relationship between a ratio of a measured phase difference to the effective thickness and the measured blood glucose concentrations; wherein the reference calibration procedure comprises the steps of:

(v) following steps (a)–(f) wherein step (d) is instead performed by passing one of the measurement and reference optical beams through a first cell of a known thickness having a first known concentration of a glucose solution and determining a first calibrated phase difference corresponding to the first known glucose solution concentration;

(vi) following steps (a)–(f) wherein step (d) is instead performed by passing one of the measurement and reference optical beams through a second cell of a known thickness having a second known concentration of a glucose solution and determining a second calibrating phase difference corresponding to the second known glucose solution concentration;

(vii) determining a reference linear relationship between the first calibrating phase difference and the second calibrating phase difference;

(viii) comparing, on the basis of a statistical correlation analysis, the reference linear relationship and the measurement relationship; and (ix) determining, on the basis of the comparison, an accuracy and resolution of measurement of blood glucose resolution.

26. The method of claim 25 in which the reference calibration procedure steps (v)–(ix) are repeated each time prior to performing steps (a)–(f) to measure blood glucose concentration non-invasively.

27. The method of claim 26 in which steps (v) and (vi) further comprise interposing a cartridge containing the first cell and the second cell in the path of the one optical beam, and selectively placing the first cell in the path of the one optical beam during step (v), placing the second cell in the path of the one optical beam during step (vi), and placing neither cell in the path of the one optical beam during step (d) for non-invasively determining the blood glucose concentration.

* * * * *

UNITED STATES PATENT AND TRADEMARK OFFICE
CERTIFICATE OF CORRECTION

PATENT NO. : 5,398,681
DATED : March 21, 1995
INVENTOR(S) : Vladimir Kupershmidt It is certified that error appears in the above-indentified patent and that said Letters Patent is hereby corrected as shown below:

Abstract, last line, after "signal." Insert --During measurement, the body tissue is inserted into the glucose sensing head (26), and after passing through the tissue, the measurement optical beam is converted into an electrical signal, compared with the reference electrical signal, and the obtained phase difference is processed by an electrical signal processing unit (30) which presents the results in the form of blood glucose concentration.--

Column 8, line 68 delete "$\vec{E}_0 e(t)$" and insert --$E_0 \vec{e}(t)$--

Column 9, line 1, delete "$e,rar/\vec{e}/_x \cos \varnothing$" and insert --$\vec{e}_x \cos \varnothing$--;

Column 17, line 63, before "optical" insert -- end --;

Column 17, line 64, delete "end";

UNITED STATES PATENT AND TRADEMARK OFFICE
CERTIFICATE OF CORRECTION

PATENT NO. : 5,398,681
DATED : March 21, 1995
INVENTOR(S) : Vladimir Kupershmidt It is certified that error appears in the above-indentified patent and that said Letters Patent is hereby corrected as shown below:

Column 18, line 6, delete "the" and insert --a--; (1st occurrence)

Column 19, line 39, after "measurement", insert --,--.

Signed and Sealed this

Eleventh Day of November, 1997

*Attest:*

BRUCE LEHMAN

*Attesting Officer*  *Commissioner of Patents and Trademarks*